United States Patent [19]

Oh-Kita et al.

[11] Patent Number: 5,093,521
[45] Date of Patent: Mar. 3, 1992

[54] PROCESS FOR PRODUCING METHACRYLIC ACID

[75] Inventors: Motomu Oh-Kita; Toru Kuroda; Yutaka Kinoshita; Kazuhiro Ishii, all of Otake, Japan

[73] Assignee: Mitsubishi Rayon Co., Ltd., Tokyo, Japan

[21] Appl. No.: 376,062

[22] Filed: Jul. 6, 1989

[30] Foreign Application Priority Data

Jul. 11, 1988 [JP] Japan .................. 63-172369

[51] Int. Cl.$^5$ .................. C07C 57/055; C07C 51/25
[52] U.S. Cl. .................. 562/534; 502/200; 502/209
[58] Field of Search ............ 562/534; 502/209, 200

[56] References Cited

U.S. PATENT DOCUMENTS

| | | | |
|---|---|---|---|
| 4,051,179 | 9/1977 | Sonobe et al. | 562/535 |
| 4,118,419 | 10/1978 | Ishii et al. | 562/534 |
| 4,146,733 | 3/1979 | White et al. | 562/535 |
| 4,341,900 | 7/1982 | Ishii et al. | 562/532 |
| 4,652,673 | 3/1987 | Matsumoto et al. | 562/535 |
| 4,803,302 | 2/1989 | Oh-Kita et al. | 562/534 |
| 4,804,778 | 2/1989 | Oh-Kita et al. | 562/534 |

FOREIGN PATENT DOCUMENTS

| | | |
|---|---|---|
| 0006248 | 6/1979 | European Pat. Off. |
| 0046333 | 2/1982 | European Pat. Off. |
| 0265733 | 5/1988 | European Pat. Off. |
| 2353131 | 4/1975 | Fed. Rep. of Germany |
| 2448804 | 4/1975 | Fed. Rep. of Germany |
| 2949545 | 6/1980 | Fed. Rep. of Germany |
| 3010434 | 11/1980 | Fed. Rep. of Germany |
| 3308625 | 9/1984 | Fed. Rep. of Germany |
| 55-2619 | 1/1980 | Japan |
| 55-122734 | 9/1980 | Japan |

Primary Examiner—Vivian Garner
Attorney, Agent, or Firm—Armstrong, Nikaido, Marmelstein, Kubovcik & Murray

[57] ABSTRACT

A process for producing methacrylic acid which includes subjecting methacrolein to gaseous phase catalytic oxidation using molecular oxygen and a catalyst represented by the general formula:

$$P_aMo_bV_cFe_dCe_e(NH_4)_fX_gY_hZ_iO_j$$

wherein P, Mo, V, Fe, Ce, NH$_4$ and O represent phosphorus, molybdenum, vanadium, iron, cerium, ammonium group and oxygen, respectively; X represents at least one element selected from the group consisting of copper, zinc, bismuth, chromium, magnesium, silver, tantalum and lanthanum; Y represents at least one element selected from the group consisting of arsenic, antimony, zirconium, barium, manganese, germanium and tellurium; Z represents at least one element selected from the group consisting of potassium, rubidium, cesium and thallium; a, b, c, d, e, g, h, i and j each represents an atomic ratio of each element, and b is 12, a is in a range of 0.5-3, c is in a range of 0.01-3, d is in a range of 0.01-2, e is in a range of 0.01-2, g is in a range of 0.01-3, h is in a range of 0.01-3, i is in a range of 0.01-2 and j is the number of oxygen atoms taken to satisfy the valence requirements stoichiometrically; f represents a number of ammonium groups and is in a range of 0.1-3.6.

3 Claims, No Drawings

PROCESS FOR PRODUCING METHACRYLIC ACID

The present invention relates to a process for producing methacrylic acid by catalytic oxidation in a gaseous phase (hereinafter, catalytic oxidation in a gaseous phase is referred to as gaseous phase catalytic oxidation).

A large number of catalysts have been heretofore proposed with regard to a process for producing an unsaturated carboxylic acid by subjecting an unsaturated aldehyde to the gaseous phase catalytic oxidation. Most of these catalysts mainly relate to a process for producing acrylic acid from acrolein. When, however, these catalysts are used for producing methacrylic acid, side reactions deteriorate the rate of selectivity of methacrylic acid and the lives of the catalysts are shortened. Therefore, the catalysts are not practical.

On the other hand, a number of catalysts have been proposed with regard to a process for producing methacrylic acid from methacrolein (for example, in Japanese Patent Application Kokai No. 55-2619, Japanese Patent Application Kokai No. 55-122734, etc.). There is, however, a drawback that these catalysts exhibit insufficient reaction achievement and sharp decrease in catalytic activity with the passage of time, and require too high reaction temperature. Therefore, they are required to be further improved for use as industrial catalysts.

The present inventors have found that a catalyst comprising a particular amount of phosphorus, molybdenum, vanadium, iron, cerium, ammonium group and the other particular elements has high catalytic activity and high selectivity and can achieve a sufficient rate of reaction even at a low reaction temperature due to the high catalytic activity, and further can maintain the high catalytic activity for a long time.

An object of the present invention is to provide an advantageous process for producing methacrylic acid from methacrolein.

Other objects and advantages of the invention will be apparent from the following description.

The present invention relates to a process for producing methacrylic acid by subjecting methacrolein to gaseous phase catalytic oxidation using molecular oxygen and a catalyst represented by the general formula:

$$P_aMo_bV_cFe_dCe_e(NH_4)_fX_gY_hZ_iO_j$$

wherein P, Mo, V, Fe, Ce, $NH_4$ and O represent phosphorus, molybdenum, vanadium, iron, cerium, ammonium group and oxygen, respectively; X represents at least one element selected from the group consisting of copper, zinc, bismuth, chromium, magnesium, silver, tantalum and lanthanum; Y represents at least one element selected from the group consisting of arsenic, antimony, zirconium, barium, manganese, germanium and tellurium; Z represents at least one element selected from the group consisting of potassium, rubidium, cesium and thallium; a, b, c, d, e, g, h, i and j each represent an atomic ratio of each element, and when b is 12, a is in a range of 0.5-3, c is in a range of 0.01-3, d is in a range of 0.01-2, e is in a range of 0.01-2, g is in a range of 0.01-3, h is in a range of 0.01-3, i is in a range of 0.01-2.and j is the number of oxygen atoms taken to satisfy the valence requirements stoichiometrically; f represents a number of ammonium groups and is in a range of 0.1-3.6 when b is 12.

The state of existence of each component element in the catalyst used in the invention is extremely complicated and has not been clarified strictly. It, however, seems that each component element exists in the form of a mixture of an oxide complex and a salt of heteropolyacid, and the ammonium group forms a double salt with the heteropolyacid and the salt thereof.

The catalyst used in the present invention can be prepared by the conventional various methods such as evaporation to dryness, precipitation and the like as long as they do not cause a considerable localization of a particular component in a lump of the catalyst.

As a raw material used in the preparation of the catalyst, there can be used an ammonium compound such as ammonium molybdate, ammonium phosphomolybdate or the like in combination with a nitrate, carbonate, ammonium salt, halide, oxide or the like of each element. Also, when the raw materials are dissolved in an aqueous ammonia in the preparation of the catalyst, the above-mentioned ammonium compound need not be used as a raw material.

The catalyst can be used without being supported on a carrier or with being supported on an inert carrier such as silica, alumina, silica-alumina, silicon carbide or the like, or diluted with said inert carrier.

In the present invention, starting materials comprise methacrolein and molecular oxygen.

The concentration of methacrolein in mixed gas of starting materials (hereinafter referred to as starting materials gas) is not critical. The concentration is preferably in a range of 1-20% by volume, more preferably 3-10% by volume.

Methacrolein, a starting material, may contain a small amount of impurities such as water, a saturated lower aldehyde and the like, which do not have any substantial influence on the reaction.

As a source of molecular oxygen, there is used air economically or, if necessary, air enriched with pure oxygen.

The concentration of oxygen in the starting materials gas is 0.3-4 parts by mole, preferably 0.4-2.5 parts by mole based on methacrolein.

The starting materials gas can contain, as a diluent(s), an inert gas(es) such as nitrogen, steam, carbon dioxide and the like.

The reaction pressure may range from normal pressure to several atmospheres.

The reaction temperature is selected from a range of 230°-450° C., preferably 250°-400° C.

The reaction can be conducted on any of a fixed bed and a fluidized bed.

The present invention is explained below more specifically referring to Examples and Comparative Examples.

The conversion of methacrolein and the selectivity for methacrylic acid are defined as follows, respectively:

Conversion of methacrolein (%) =

Selectivity of methacrylic acid (%) =

-continued $$\frac{\text{Moles of methacrylic acid produced}}{\text{Moles of methacrolein reacted}} \times 100$$

In the following Examples and Comparative Examples part(s) represents part(s) by weight, and analyses were conducted by gas chromatography.

EXAMPLE 1

In 300 parts of pure water were dissolved 100 parts of ammonium paramolybdate, 2.8 parts of ammonium metavanadate and 4.8 parts of potassium nitrate. Thereto were added the solution obtained by dissolving 8.2 parts of 85%-phosphoric acid in 10 parts of pure water, and further 3.4 parts of antimony trioxide. The mixture was heated to 95° C with stirring.

To the mixture, further, was added a mixture obtained by adding 1.14 parts of cupric nitrate, 0.81 part of cerium dioxide and 5.7 parts of ferric nitrate to 30 parts of pure water. The resulting mixture liquid was evaporated to dryness by heating at 100° C. with stirring.

The obtained solid matter was dried at 130° C. for 16 hours, and thereafter, molded by pressing, heat-treated at 380° C. for 5 hours, and then used as the catalyst.

The composition of the obtained catalyst, represented using elements other than oxygen (hereinafter the composition of the catalyst is represented using elements other than oxygen) was as follows:

$P_{1.5}Mo_{12}V_{0.5}Fe_{0.3}Ce_{0.1}Cu_{0.1}Sb_{0.5}K_1(NH_4)_{0.6}$

This catalyst was filled in a reactor. A mixed gas of 5% by volume of methacrolein, 10% by volume of oxygen, 30% by volume of steam and 55% by volume of nitrogen was allowed to pass through the reactor at a reaction temperature of 270° C. in a contact time of 3.6 sec. The product was collected and analyzed by gas chromatography. As a result, the conversion of methacrolein was 89.0% and the selectivity for methacrylic acid was 87.6%.

EXAMPLES 2-10

The same procedures were repeated as Example 1, except that catalysts shown in Table 1 were prepared. The results are shown in Table 1.

COMPARATIVE EXAMPLE 1

The same procedure was repeated as Example 1, except that ferric nitrate and cerium dioxide were not used and the catalyst represented by the formula:

$P_{1.5}Mo_{12}V_{0.5}Cu_{0.1}Sb_{0.5}K_1(NH_4)_{0.6}$ was prepared as a comparative catalyst. As a result, the conversion of methacrolein was 80.3% and the selectivity for methacrylic acid was 80.1%.

COMPARATIVE EXAMPLE 2

To pure water were added molybdenum trioxide, vanadium pentaoxide, phosphoric acid, antimony trioxide, cupric oxide, cerium dioxide and iron (III) oxide. The mixture was refluxed by heating for 6 hours. To the mixture was added potassium hydroxide. The resulting mixture was refluxed by heating further for 3 hours and thereafter evaporated to dryness.

The obtained solid matter was treated in the same manner as in Example 1 to prepare a catalyst containing no ammonium group represented by the following formula:

$P_{1.5}Mo_{12}V_{0.5}Fe_{0.3}Ce_{0.1}Cu_{0.1}Sb_{0.5}K_1$

The production of methacrylic acid was conducted in the same manner as in Example 1. As a result, the conversion of methacrolein was 77.1% and the selectivity for methacrylic acid was 87.0%.

TABLE 1

| Example | Catalyst composition | Conversion of methacrolein (%) | Selectivity for methacrylic acid (%) |
|---|---|---|---|
| 2 | $P_{1.5}Mo_{12}V_{0.5}Fe_{0.3}Ce_{0.1}Cu_{0.1}Zn_{0.1}Ge_{0.3}Cs_1(NH_4)_{0.2}$ | 90.1 | 86.9 |
| 3 | $P_{1.5}Mo_{12}V_1Fe_{0.1}Ce_{0.3}Bi_{0.1}As_{0.1}Mn_{0.08}Tl_{0.8}(NH_4)_{0.5}$ | 89.5 | 87.4 |
| 4 | $P_2Mo_{12}V_1Fe_{0.1}Ce_{0.3}Cu_{0.1}La_{0.1}Te_{0.1}Rb_1(NH_4)_{0.6}$ | 88.4 | 87.9 |
| 5 | $P_2Mo_{12}V_1Fe_{0.3}Ce_{0.1}Cu_{0.2}Cr_{0.1}Zr_{0.1}K_{0.3}Cs_{0.6}(NH_4)_{0.3}$ | 90.0 | 86.6 |
| 6 | $P_{1.5}Mo_{12}V_{0.5}Fe_{0.1}Ce_{0.3}Cu_{0.1}Ag_{0.05}Te_{0.1}Ba_{0.1}K_1(NH_4)_{0.8}$ | 89.2 | 87.6 |
| 7 | $P_{1.5}Mo_{12}V_{0.5}Fe_{0.3}Ce_{0.1}Mg_{0.1}Sb_1K_1(NH_4)_{1.1}$ | 87.4 | 88.0 |
| 8 | $P_{1.5}Mo_{12}V_{0.5}Fe_{0.2}Ce_{0.3}Cu_{0.1}Ta_{0.1}Sb_{0.5}K_1(NH_4)_{0.8}$ | 89.3 | 87.7 |
| 9 | $P_1Mo_{12}Fe_{0.5}Ce_{0.1}Zn_{0.1}La_{0.4}As_{0.1}K_1(NH_4)_{0.8}$ | 86.6 | 88.3 |
| 10 | $P_1Mo_{12}V_1Fe_{0.1}Ce_{0.5}Cu_{0.2}Zn_{0.1}Ta_{0.1}Ge_{0.1}K_1(NH_4)_{0.4}$ | 89.3 | 87.5 |

What is claimed is:

1. A process for producing methacrylic acid which comprises subjecting methacrolein to gaseious phase catalytic oxidation at a temperature in a range of 230°–450° C. using molecular oxygen and a catalyst represented by the general formula:

$P_aMo_bV_cFe_dCe_e(NH_4)_fX_gY_hZ_iO_j$ wherein P, Mo, V, Fe, Ce, NH$_4$ and O represent phosphorus, molybdenum, vanadium, iron, cerium, ammonium group and oxygen, respectively; X represents at least one element selected from the group consisting of copper, zinc, bismuth, chromium, magnesium, silver, tantalum and lanthanum; Y represents at least one element selected from the group consisting of arsenic, antimony, zirconium, barium, manganese, germanium and tellurium; Z represents at least one element selected from the group consisting of potassium, rubidium, cesium and thallium; a, b, c, d, e, g, h, i and j each represent an atomic ratio of each element, and b is 12, a is in a range of 0.5–3, c is in a range of 0.01–3, d is in a range of 0.01–2, e is in a range of 0.01–2, g is in a range of 0.01–3, h is in a range of 0.01–3, i is in a range of 0.01–2 and j is the number of oxygen atoms taken to satisfy the valence requirements stoichiometrically; f represents the number of ammonium groups and is in a range of 0.1–3.6.

2. A process for producing methacrylic acid according to claim 1, wherein the concentration of methacrolein in starting material gas is in a range of 1–20% by volume and the concentration of oxygen in starting materials gas is in a range of 0.3–4 parts by mole based on methacrolein.

3. A process for producing methacrylic acid according to claim 1, wherein the concentration of methacrolein in starting materials gas is in a range of 3–10% by volume, the concentration of oxygen in starting materials gas is in a range of 0.4–2.5 parts by mole based on methacrolein, and the reaction temperature is in a range of 250°–400° C.

* * * * *